US00PP23636P3

(12) United States Plant Patent
Blom

(10) Patent No.: US PP23,636 P3
(45) Date of Patent: May 28, 2013

(54) ***CHRYSANTHEMUM* PLANT NAMED 'ZANMUEMBER'**

(50) Latin Name: ***Chrysanthemum×morifolium* Ramat.**
Varietal Denomination: Zanmuember

(75) Inventor: Wilhelmus Bernardus Blom, Leimuiden (NL)

(73) Assignee: Chrysanthemum Breeders Association Research B.V., Valkenburh Z-H (NL)

( * ) Notice: Subject to any disclaimer, the term of this patent is extended or adjusted under 35 U.S.C. 154(b) by 89 days.

(21) Appl. No.: 13/200,326

(22) Filed: Sep. 23, 2011

(65) Prior Publication Data
US 2013/0081162 P1 Mar. 28, 2013

(51) Int. Cl.
*A01H 5/00* (2006.01)

(52) U.S. Cl.
USPC ..... Plt./295

(58) Field of Classification Search ..... Plt./295
See application file for complete search history.

*Primary Examiner* — Annette Para
(74) *Attorney, Agent, or Firm* — Steptoe & Johnson LLP

(57) ABSTRACT

A *chrysanthemum* plant named 'Zanmuember' characterized by its medium sized blooms with bronze ray florets and prolific branching; natural season flower date week 41; blooming for a period of 4 weeks.

3 Drawing Sheets

Botanical designation: *Chrysanthemum×morifolium* Ramat.
Cultivar denomination: 'Zanmuember'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuember'. 'Zanmuember' is a product of a breeding and selection program for outdoor pot mums (garden mums) which had the objective of creating new cultivars with a double type inflorescence, a natural season flower date around week 41, blooming for a period of 5 weeks. 'Zanmuember' is a seedling resulting from a cross of the female parent id 9376 with the male parent id 177772. Both parents are unpatented plants. Plants of the new cultivar 'Zanmuember' differ from plants of the female parent in the following characteristics. (1) Plant vigor and (2) Natural season flower date. (1) Plants of the seedling are more vigorous than plants of the female parent. (2). Plants of the seedling flower later in season than plants of the female parent. Plants of the new cultivar 'Zanmuember' differ from plants of the male parent in the following characteristics. (1) Inflorescence size and (2) Natural season flower date. (1). The size of the inflorescences of the seedling is larger than those of the male parent. (2). Plants of the seedling flower later in season than plants of the male parent.

The new and distinct cultivar was discovered and selected as a flowering plant by Wilhelmus Bernardus Blom on a cultivated field in Rijsenhout, The Netherlands in 2005. The first act of asexual production of 'Zanmuember' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct cultivar of *chrysanthemum* is shown in the accompanying drawings, the color being as nearly true as possible with color photographs of this type.

DESCRIPTION OF THE INVENTION

Figure 1:
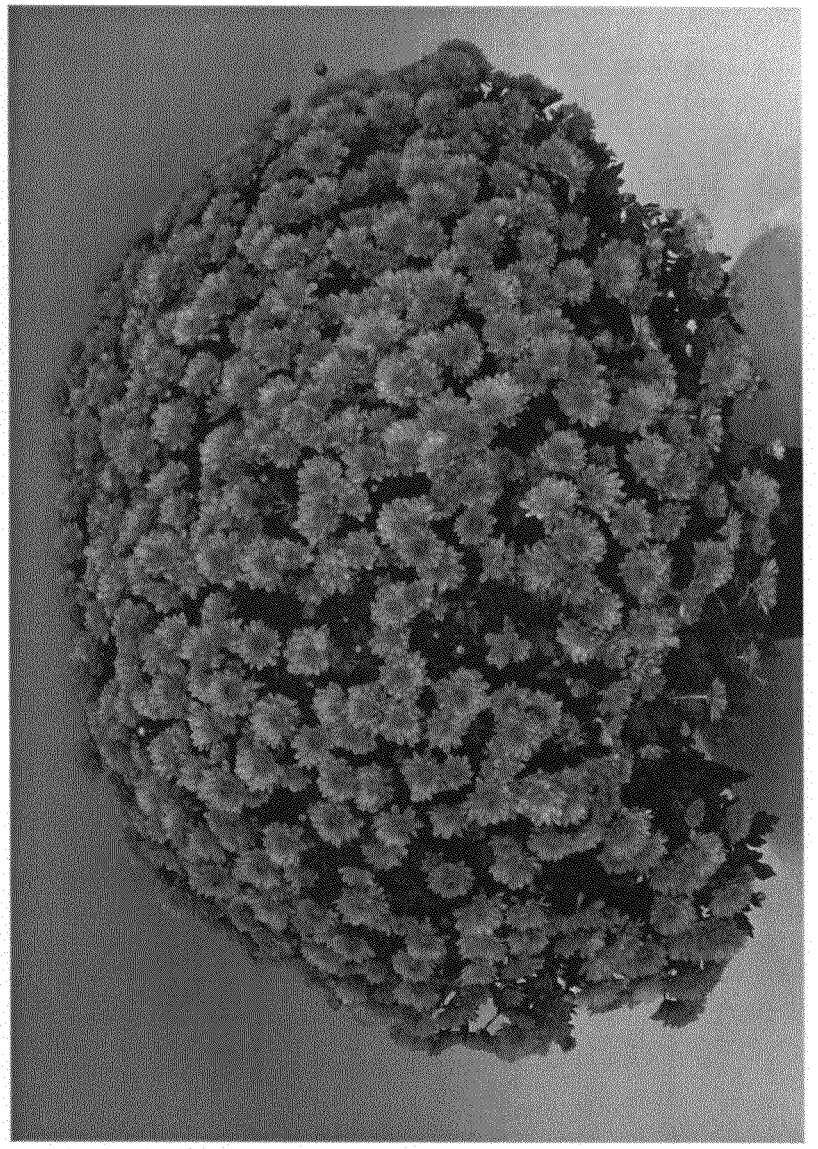
FIG. 1 shows a plant of the cultivar in full bloom.
Figure 2:
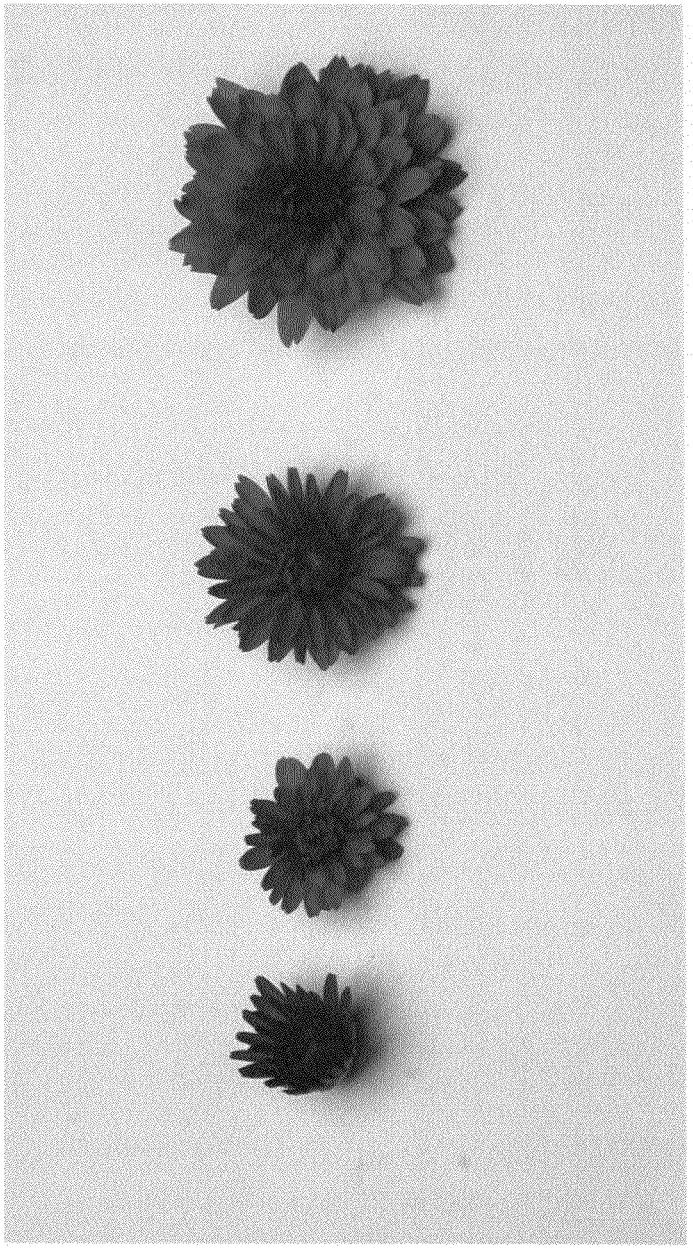
FIG. 2 shows the various stages of bloom of the new cultivar.
Figure 3:
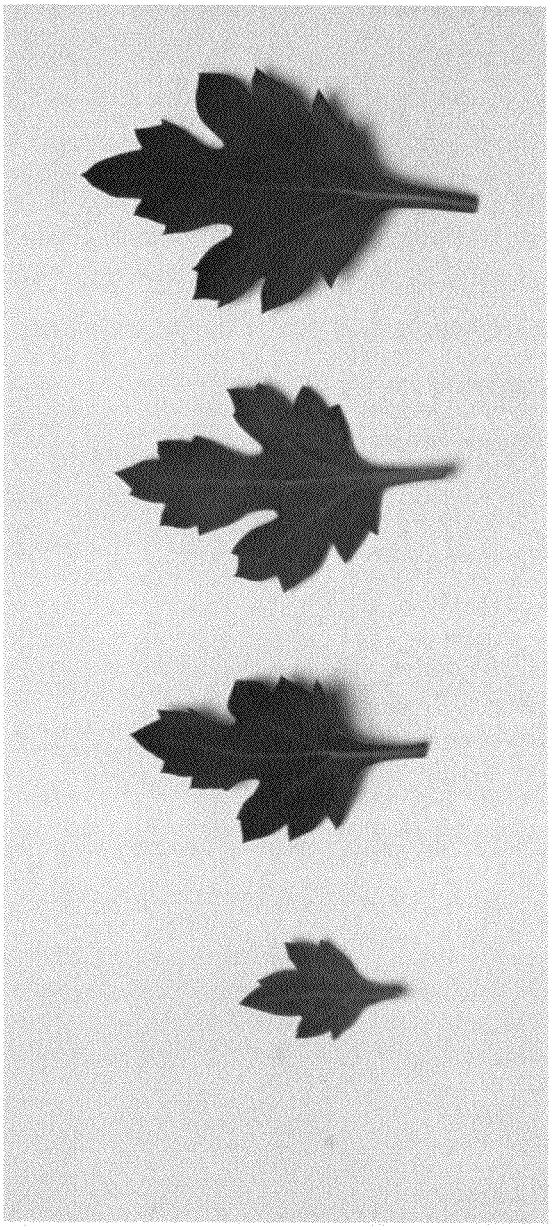
FIG. 3 shows the various stages of foliage of the new cultivar.

The observations and measurements were gathered from plants grown out door in Rijsenhout, The Netherlands under natural day length and temperature and planted in week 23 in 2010. The natural blooming date of this crop was October 11 (week 41). The average height of the plants was 39 cm. No growth retardants were used. No tests were done on disease or insect resistance or susceptibility. No tests were done on cold or drought tolerance. This new cultivar produces medium sized blooms with bronze ray florets blooming for a period of 4 weeks.

From the cultivars known to inventor the most similar existing cultivars in comparison to 'Zanmuember' are 'Zanmusunset' (U.S. Plant Pat. No. 20,475) and 'Zanmufay'(U.S. Pat. No. 22,336). When 'Zanmuember' is being compared with 'Zanmusunset' and 'Zanmufay' the following differences are noticed (1) Color upper surface of ray florets. And (2) Presence of a disc in inflorescences. (1) The orange color of the upper surface of the ray florets is more yellow in tone in 'Zanmufay' than in 'Zanmuember' and 'Zanmusunset'. (2) A small disc is present in the inflorescences of 'Zanmuember', while it is absent in 'Zanmusunset' and 'Zanmufay'.

The following is a description of the plant and characteristics that distinguish 'Zanmuember' as a new and distinct cultivar.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Detailed Botanical Description | |
|---|---|
| **Bud** | |
| Size | Small; cross-section 5 mm, height 4 mm |
| Shape | Round |
| Texture | Pubescent |
| Outside Color | Greyed-green 191A |
| **Phyllaries** | |
| Number | 20, arranged in 3 rows |
| Shape | Elliptic |
| Apex | Acute |
| Base | Truncate |
| Margin | Entire |
| Color | Upper surface: Green 138A<br>Lower surface: Green 138B |
| Length and width | 4 mm; 2 mm |
| Texture | Pubescent |
| **Inflorescences** | |
| Type | Double |
| Height | 1.2 cm |
| Diameter | 5 cm |
| Peduncle length | 4-5 cm |
| Peduncle color | Green 138B |
| Peduncle diameter | 1 mm |
| Peduncle texture | Pubescent |
| Number per branch | Approx. 5 inflorescences |
| Duration of flowering | 4 weeks |
| Seeds | Produced in small quantities, ovate, Greyed-brown 199A, length 1.5 mm, diameter 0.5 mm |
| Fragrance | Faint chrysanthemum odor |
| **Color** | |
| Center of inflorescence | Immature stage: Greyed-red 178B<br>Mature stage: Yellow 12C |
| Color of upper surface of the ray-florets | Greyed-orange 168B to 168C |
| Color of the lower surface of the ray-florets | Greyed-orange 167D |
| Tonality from Distance | A garden mum with bronze blooms and a dark center |
| Color of the ray-florets after aging of the plant | Greyed-orange 168D |
| **Ray florets** | |
| Texture | Upper and lower surface smooth |
| Number | 210-230 |
| Shape | Elliptic |
| Apex | Dentate |
| Base | Attnuate |
| Cross-section | Flat |
| Longitudinal axis of majority | Straight |
| Length of corolla tube | 3-4 mm |
| Ray-floret margin | Entire |
| Ray-floret length | 1.8-2 cm |
| Ray-floret width | 4-6 mm |
| Ratio length/width | High |
| **Disc florets** | |
| Disc diameter | 1 cm |
| Distribution of disc florets | Scarce |
| Shape | Tubular |
| Color | Yellow-green 150D at base to Yellow 12C at apex |
| Length | 4 mm |
| Diameter | 3 mm |
| **Receptacle** | |
| Color | Yellow-green 145D |
| Shape | Conical raised |
| Height | 4 mm |
| Diameter | 3 mm |

TABLE 1-continued

| Detailed Botanical Description | |
|---|---|
| **Reproductive Organs** | |
| Androecium | Present on only disc florets |
| Stamen length | 3 mm |
| Stamen color | Yellow-green 144A |
| Anther color | Yellow 3A |
| Pollen | Present |
| Pollen color | Yellow 13A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| **Plant** | |
| Form | Grown as a spray type pot mum, outdoor raised and mounded |
| Growth habit | Spherical shape |
| Growth rate | High |
| Height | 38-40 cm |
| Width | 60 cm |
| Stem Color | Greyed-brown 199A |
| Stem Strength | Strong |
| Stem Brittleness | Not brittle |
| Stem Anthocyanin Coloration | Not observed |
| Internode length | 1.5-2 cm |
| Length of lateral branch | From top to bottom 22 cm |
| Lateral branch color | Green 137C |
| Lateral branch, attachment | Brittle |
| Lateral branch diameter | 22 mm |
| Branching (average number of lateral branches) | Prolific with 7 breaks after pinching |
| Natural season blooming date | October 11 (week 41) |
| **Foliage** | |
| Leaf color | Upper side: Green 137A<br>Lower side: Green N138C |
| Color midvein | Upper side: Yellow-green 147D<br>Lower side: Yellow-green 148D |
| Size | Small; length 2-5.5 cm, width 1-3 cm |
| Quantity (number per lateral branch) | 16-18 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronulate |
| Petiole length | 1-2 cm |
| Petiole diameter | 2 mm |
| Petiole color | Yellow-green 147D |

TABLE 2

| Differences with the comparison cultivars | | | |
|---|---|---|---|
| | 'Zanmuember' | 'Zanmusunset' | 'Zanmufay' |
| Color upper surface ray floret | Greyed-Orange 168B to 168C | Greyed-Orange 168B to 168C | Greyed-Orange 163B to 163D |
| Presence disc in inflorescences | Present | Absent | Absent |

I claim:

1. A new and distinct *chrysanthemum* plant named 'Zanmuember' as described and illustrated.

* * * * *